(12) United States Patent
Henry et al.

(10) Patent No.: US 10,845,334 B2
(45) Date of Patent: Nov. 24, 2020

(54) CELL EXTRACTION USING GEITP

(71) Applicant: Applied Research Associates, Inc., Albuquerque, NM (US)

(72) Inventors: Alyssa C. Henry, Arlington, VA (US); Vanessa M. Thomas, Albuquerque, NM (US)

(73) Assignee: Applied Research Associates, Inc., Albuquerque, NM (US)

( * ) Notice: Subject to any disclaimer, the term of this patent is extended or adjusted under 35 U.S.C. 154(b) by 0 days.

(21) Appl. No.: 16/265,454

(22) Filed: Feb. 1, 2019

(65) Prior Publication Data

US 2020/0249200 A1 Aug. 6, 2020

(51) Int. Cl.
*C12N 1/00* (2006.01)
*G01N 27/447* (2006.01)
*B01L 3/02* (2006.01)
*C12N 1/02* (2006.01)

(52) U.S. Cl.
CPC ........ *G01N 27/44791* (2013.01); *B01L 3/022* (2013.01); *C12N 1/02* (2013.01); *G01N 27/4473* (2013.01); *G01N 27/44721* (2013.01); *G01N 27/44743* (2013.01); *B01L 2400/025* (2013.01); *B01L 2400/0406* (2013.01)

(58) Field of Classification Search
CPC ...... C12N 1/00; C12N 1/02; G01N 27/44791; G01N 27/44743; G01N 27/44739
See application file for complete search history.

(56) References Cited

U.S. PATENT DOCUMENTS

| 8,080,144 | B2 | 12/2011 | Ross et al. |
| 8,366,897 | B2 | 2/2013 | Ross et al. |
| 10,067,088 | B2 | 9/2018 | Henry et al. |

OTHER PUBLICATIONS

Phung et al., "Isotachophoretic Fluorescence in Situ Hybridization of Intact Bacterial Cells," Anal. Chem.. 2017, 89, 6513-6520 (Year: 2017).*

* cited by examiner

*Primary Examiner* — Alexander S Noguerola
(74) *Attorney, Agent, or Firm* — Erise IP, P.A.

(57) ABSTRACT

A cell extraction method includes providing a mixed-cell sample having both target cells and non-target cells slurried in a trailing-electrolyte solution. A leading electrolyte solution is provided to contact the trailing electrolyte solution via a capillary and a pressure control device. Focusing of the target cells at an interface between the leading- and trailing-electrolyte solutions occurs by applying pressure to the capillary and concurrently applying an electric potential via electrodes. The target cells are extracted into the capillary by applying a negative pressure and transferred to a receptacle. A cell extraction system for use with a gradient elution isotachophoresis method includes a trailing electrolyte solution adapted to migrate slower than the target cells and a leading electrolyte solution adapted to migrate faster than the target cells. A mixed-cell sample containing the target and non-target cells is slurried in the trailing electrolyte solution prior to cell extraction.

20 Claims, 3 Drawing Sheets

CELL EXTRACTION USING GEITP

BACKGROUND

1. Field

Embodiments of this disclosure relate generally to electrophoretic separation techniques. More specifically, embodiments of this disclosure relate to a method for separating cells based on gradient elution isotachophoresis (GEITP).

2. Related Art

Various methods for separating compounds from a mixture using GEITP have been described. U.S. Pat. No. 8,080,144 to Ross et al. discloses a gradient elution electrophoresis method for separating ionic compounds. U.S. Pat. No. 8,366,897 to Ross et al. and U.S. Pat. No. 10,067,088 to Henry et al. disclose an apparatus for gradient elution electrophoresis.

SUMMARY

Embodiments of this disclosure provide methods for separating cells of a particular type from a mixed-cell sample containing more than one type of cells based on gradient elution isotachophoresis (GEITP). Embodiments disclosed herein also describe buffer solutions (e.g., leading and trailing electrolyte solutions) adapted for separating a desired cell type from a mixed-cell sample using GEITP. Certain embodiments disclosed herein are particularly useful for processing sexual assault kits by forensics labs, in which sperm cells are to be separated from other cell types (e.g., epithelial cells) prior to conducting further analysis, such as DNA analysis.

A first embodiment is directed to a cell extraction method. The cell extraction method includes providing a mixed-cell sample in a sample container, the mixed-cell sample having both target cells and non-target cells slurried in a trailing-electrolyte solution. The method further includes providing a leading-electrolyte solution in a capillary, the capillary having an inlet and an outlet, the inlet being coupled with a pressure control device and the outlet being disposed in the sample container. The method further includes focusing the target cells at an interface between the leading-electrolyte solution and the trailing-electrolyte solution by applying a positive pressure to the inlet of the capillary via the pressure control device, and by concurrently applying an electric field along the length of the capillary via electrodes. The method further includes extracting the target cells from the sample container and into the capillary by applying a negative pressure to the inlet of the capillary. The method concludes with expelling the target cells into a receptacle by transferring the capillary from the sample container to the receptacle and then applying a positive pressure to the inlet with the pressure control device.

A second embodiment is directed to a cell extraction system for use with a gradient elution isotachophoresis method. The system includes a trailing electrolyte solution adapted to migrate slower than target cells while using the gradient elution isotachophoresis method. A mixed-cell sample containing the target cells and non-target cells is slurried in the trailing electrolyte solution prior to cell extraction. A leading electrolyte solution is adapted to migrate faster than the target cells while using the gradient elution isotachophoresis method. The leading electrolyte solution is provided to a separation path in fluid contact with the trailing electrolyte solution.

Another embodiment may be directed to extracting sperm cells from samples of a sexual assault kit using gradient elution isotachophoresis. The sperm cells may be isolated, separated, concentrated, detected, and/or quantified directly from the sexual assault kit samples enabling such analysis as male DNA analysis.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages will be apparent from the following detailed description of the embodiments and the accompanying drawing figures.

BRIEF DESCRIPTION OF THE DRAWING FIGURES

Embodiments of this disclosure are described in detail below with reference to the attached drawing figures, wherein.

Figure 1:
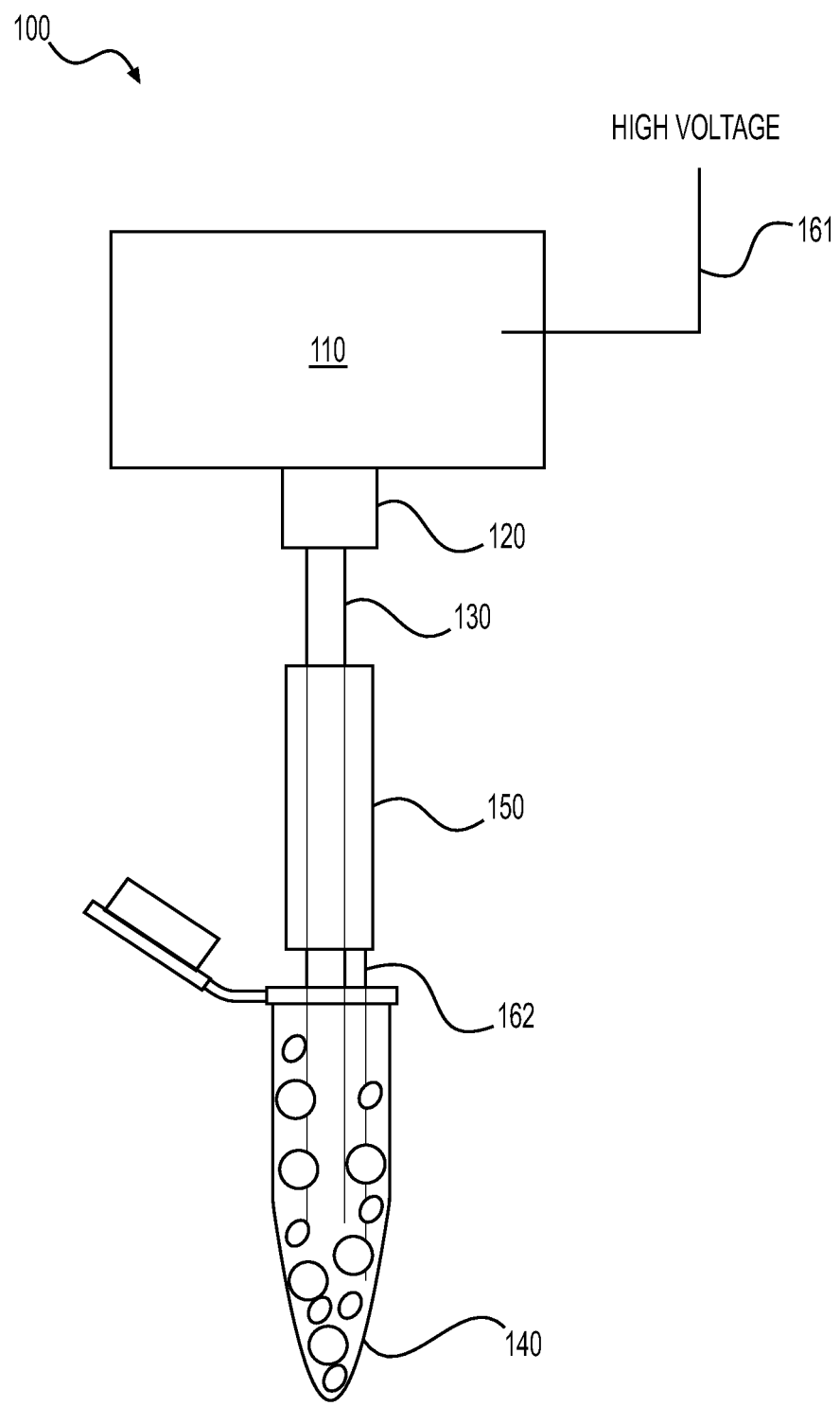
FIG. 1 is a diagram illustrating a GEITP system adapted for extracting a target cell type from a sample of mixed cell types, in an embodiment.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the present disclosure provide methods for separating cells of a desired type (e.g., target cells) from a mixed-cell sample (e.g., having cells of more than one type) based on gradient elution isotachophoresis (GEITP). Isotachophoresis is a type of electrophoresis in which electrolytes having differing electrophoretic mobility are used. A leading electrolyte (LE) migrates faster through an applied electric field compared to a trailing (or terminating) electrolyte (TE). An analyte having an electrophoretic mobility between that of the LE and the TE becomes focused at the interface between the LE and the TE. Hydrodynamic pressure may be applied to migrate the LE/TE interface into a separation path (e.g., a capillary) where it may then be analyzed using an appropriate detector. Subsequently, the hydrodynamic pressure may be reversed to transfer the focused analyte to a separate container for subsequent analysis. Certain embodiments described herein are particularly useful for processing sexual assault kits by forensics labs, where sperm cells need to be separated from other cell types (e.g., epithelial cells) prior to conducting further analysis, such as lysis followed by DNA analysis.

FIG. 1 shows a diagram illustrating a GEITP system 100 adapted for extracting a particular type of cells (e.g., the target cells) from a mixed-cell sample containing more than one cell type. In certain embodiments, system 100 includes a GEITP apparatus as described in U.S. Pat. No. 10,067,088 to Henry et al., which is incorporated by reference in its entirety.

In general, system 100 includes a LE reservoir 110 for storing an appropriate volume of a LE solution. The LE solution is adapted to have a faster electrophoretic mobility compared to the target cells to be separated. In some embodiments, the LE solution is a 1000 mM tris(hydroxymethyl)aminomethane (Tris) and 400 mM tartrate solution. Other negative anions besides tartrate may be used, such as chloride, acetate, etc., without departing from the scope hereof.

A pump 120 is coupled to the LE reservoir 110 for applying positive or negative pressure for driving fluid flow. Pump 120 is a pressure control device, such as a syringe pump having one or more pressure-stepper motors coupled with a pressure gauge. Pump 120, which is capable of delivering small volumes of fluid, uses pneumatic pressure to drive fluid flow in a separation path. In certain embodiments, the separation path is provided via a capillary 130.

Capillary 130 is, for example, a fused silica capillary tube having a predetermined size chosen for selectively accepting the target cell type at the exclusion of other (e.g., larger) cell types, as well as a proficiency to receive a large number of target cells. For example, an inner diameter (ID) of capillary 130 may be in the range of about 5 µm to about 100 µm. In certain embodiments, the capillary ID is about 10 µm, 15 µm, 24 µm, 30 µm, 40 µm, 50 µm or 75 µm. A length of capillary 130 may be from about 1 cm to about 15 cm. In some embodiments, the length of capillary 130 is about 9 cm. Other capillary materials, IDs, and lengths may be used without departing from the scope hereof.

In certain embodiments, capillary 130 is a single-bore capillary; however, multi-bore capillaries may be used without departing from the scope hereof. For example, a 16-bore or 24-bore capillary may be used for extracting about 16- or 24-times the number of target cells, depending on the target cell concentration, which may be useful to provide enough cells to perform certain types of subsequent analysis (e.g., DNA analysis after cell lysis).

A sample container 140 contains a mixed-cell sample that includes cells suspended in a buffer solution from which the target cells are to be separated, concentrated, and extracted, as further described below in connection with FIGS. 2A-2D and FIG. 3. Any cells in the mixed-cell sample that are not the target cells are considered "non-target" cells. Prior to extraction of the target cells, sample container 140 is placed such that capillary 130 is fluidly in contact with the mixed-cell sample. In certain embodiments, the buffer solution in which the mixed-cell sample is slurried or suspended is a TE solution having an electrophoretic mobility that is slower than the target cells. In an embodiment, the TE solution is a 12.5 mM Tris-HEPES buffer solution having 12.5 mM of Tris and 12.5 mM of 4-(2-hydroxyethyl)-1-piperazineethanesulfonic acid (HEPES).

A detector 150 is located adjacent a portion of capillary 130 for detecting the presence of cells within the capillary. In certain embodiments, detector 150 is a capacitively-coupled contactless conductivity detector ($C^4D$) or a laser-induced fluorescence (LIF) detector. In some embodiments, detector 150 includes both a $C^4D$ and a LIF detector, which are further described below in connection with FIG. 2C.

LE reservoir 110 is electrically coupled to a voltage control device (not shown) for providing an electric potential between LE reservoir 110 and the sample. In certain embodiments, a first electrode 161 is a high-voltage (e.g., about 1000V to 2000V) electrode at positive polarity placed in LE reservoir 110, while a second electrode 162 is an anode or grounded electrode placed in sample container 140. In certain embodiments, the polarity of first electrode 161 may be flipped to detect different types of cells.

A controller (not shown) may be used to provide control of one or more components of system 100, including pump 120, the voltage control device, and detector 150. The controller includes a processor and a memory for storing software as machine readable instructions that are executable by the processor. The controller is for example one or more of a server, a computer, a microcontroller, or a programmable logic controller (PLC). The memory in some embodiments is a memory system that includes both transitory memory such as RAM and non-transitory memory such as, ROM, EEPROM, Flash-EEPROM, magnetic media including disk drives, and optical media. In certain embodiments, the controller is a computer running LabView software, and one or more components of system 100 (e.g., pump 120, the voltage control device, and/or detector 150) are National Instruments input/output devices that are controllable via the LabView software.

In certain embodiments, a moveable support structure (not shown) may be attached to components of system 100 for enabling parts of system 100 to be moved. For example, the moveable support structure may be used to move the extraction assembly (e.g., LE reservoir 110, pump 120, and capillary 130) for transferring capillary 130 from sample container 140 to another container. In some embodiments, the moveable support structure may be further adapted to move detector 150 (e.g., to and from capillary 130).

FIGS. 2A, 2B, 2C, and 2D show system 100 at various steps in operation. Prior to extraction, a mixed-cell sample is provided in a sample container. The mixed-cell sample includes cells from a mixture of cell types, including a target cell type and at least one other (e.g., non-target) cell type.

The mixed-cell sample is suspended or slurried-in the TE solution. The cells in the solution are allowed to settle for 10-15 min prior to extraction.

Figure 2:
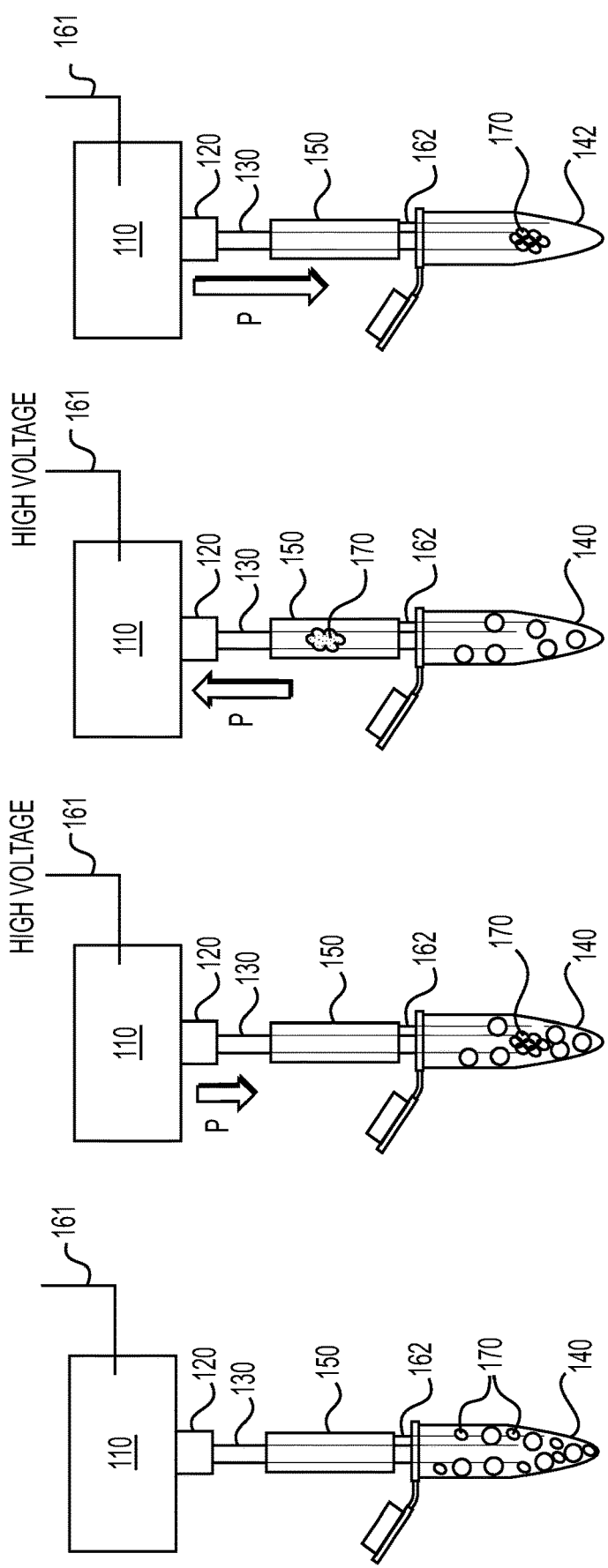
FIG. 2A shows the GEITP system of FIG. 1 in an initial step of operation in which a capillary and an electrode are placed in a mixed-cell sample, in an embodiment.
FIG. 2B shows the GEITP system of FIG. 1 in a subsequent step of operation for focusing target cells, in an embodiment.
FIG. 2C shows the GEITP system of FIG. 1 in a subsequent step of operation for extracting the target cells, in an embodiment.
FIG. 2D shows the GEITP system of FIG. 1 in a final step of operation for eluting the target cells, in an embodiment.

As depicted in FIG. 2A, capillary 130 and second electrode 162 are placed in the sample container containing the mixed-cell sample in the TE solution.

As depicted in FIG. 2B, the target cell type is focused at the LE/TE interface. A small positive hydrodynamic pressure (P) is applied from pump 120 to drive LE solution from LE reservoir 110 downward through capillary 130 such that a small amount of LE buffer enters sample container 140. For example, the pressure is slowly ramped up by about 700 Pa during the focusing step. Concurrently, an electric potential is applied between the electrodes, which is maintained through detection (FIG. 2C). In certain embodiments, the electric potential is from about 1000V to about 2000V, depending on the ID of capillary 130. The maximum electrical current resulting from the applied electrical potential is typically from 5 µA to about 50 µA depending on the capillary ID, among other things. In certain embodiments, the maximum electrical current is about 8 µA, 10 µA, 12 µA, 15 µA, or 30 µA. The electric potential produces an electric field causing the target cells to migrate towards the LE/TE interface. A higher maximum current often provides a faster migration rate. In certain embodiments, a pressure-driven counter flow of LE solution through capillary 130 is provided via pump 120, which may assist with separating target cells from non-target cells.

Over time, the target cells focus at the LE/TE interface. The amount of time for focusing of the target cells at the LE/TE interface may be varied based on many factors such as the sample volume, the density of target cells, the concentration of electrolytes in the LE and TE solutions, the maximum electrical current applied, and the pressure-driven counterflow provided via pump 120, etc. An amount of time for focusing the target cells is typically from about five minutes to about thirty minutes. In certain embodiments, the focusing time is five, seven, ten, fifteen, or twenty minutes. Other focusing times may be used without departing from the scope hereof.

As depicted in FIG. 2C, focused cells 170 are pulled into capillary 130 for detection. Following focusing, a moderate negative hydrodynamic pressure (P) is applied from pump 120 to extract focused cells 170 from the sample and draw them upwards into capillary 130 to the region adjacent detector 150. The negative pressure applied is typically about −2500 Pa.

In certain embodiments, detector 150 is adapted to detect the transition from the LE solution to the TE solution as the LE/TE interface is pulled through the capillary past the detector. For example, conductivity detection (e.g., via $C^4D$) detects a difference in conductivity between the LE solution and the TE solution. Since target cells 170 are focused at the LE/TE interface, the conductivity detector is used to indirectly determine that focused cells 170 are located in capillary 130.

In some embodiments, the LIF detector is used to detect the focused cells directly. Laser light is used to illuminate a portion of the capillary, and emitted light is received by a photodetector. The target cells may be labeled with light-excitable dye selected to match the excitation wavelength of laser light. As the target cells are illuminated, the dye is excited causing it to emit light at a longer wavelength which is received by the photodetector. One or more filters may be used in conjunction with the photodetector for receiving the emitted light within a targeted emission spectrum. An intensity of the emission spectrum may be correlated with a number of cells to estimate the number of target cells 170 in capillary 130.

As depicted in FIG. 2D, target cells 170 are delivered to a receptacle 142. Following detection, sample container 140 is removed from capillary 130 and replaced with receptacle 142, which is a clean receptacle lacking any cells. A large positive hydrodynamic pressure (e.g., about 4000 Pa) is applied by pump 120 to expel target cells 170 into receptacle 142, which may contain a buffer solution or a preservation solution to prepare the cells for subsequent analysis. Subsequent analysis may include, but is not limited to, staining the cells for counting by light microscopy, lysing the cells for DNA extraction, DNA sequence identification and quality determination (e.g., qPCR, short-tandem repeat typing, etc.).

Figure 3:
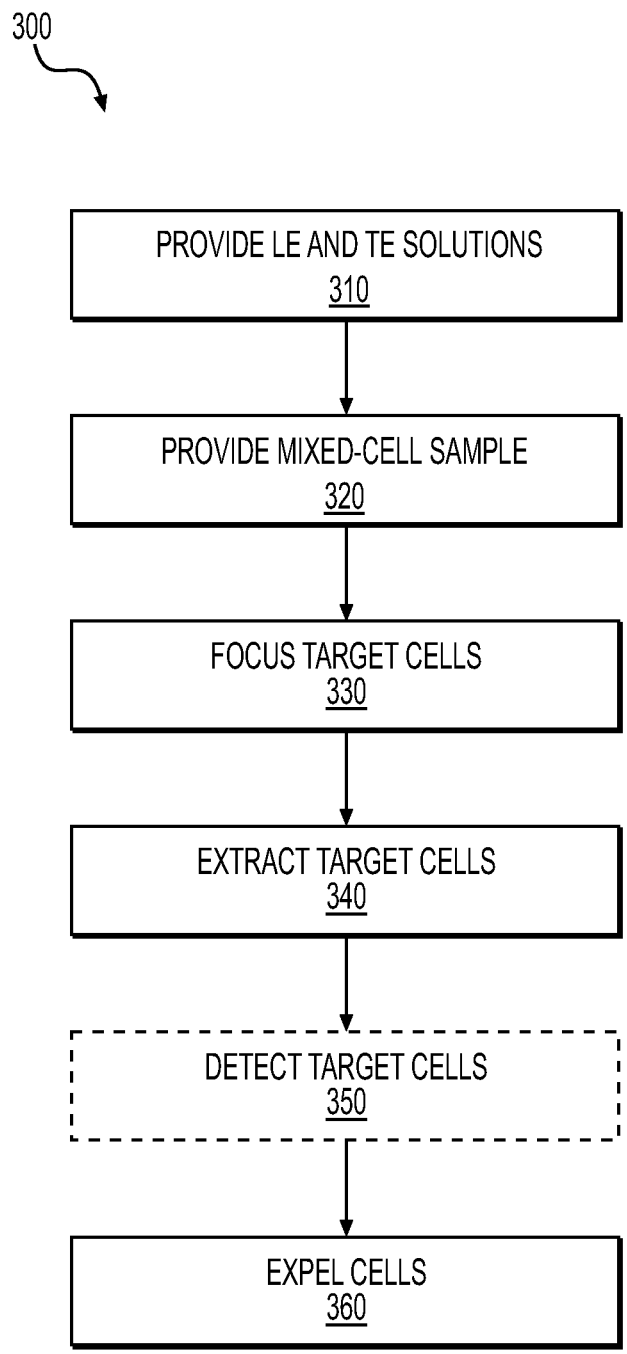
FIG. 3 shows steps of a method for extracting target cells from a mixed-cell sample using GEITP, in an embodiment.

FIG. 3 shows steps of a method 300 for sperm cell (spermatozoa) extraction from a sample of mixed cell types based on GEITP. Method 200 may be performed using system 100, FIG. 1, for example.

In a Step 310, the LE solution and the TE solution are provided. Depending on the electrophoretic mobility of the cells to be extracted, a LE solution is formulated for migrating faster than the target cells, and a TE solution is formulated for migrating slower than the target cells, when an electric field is applied. The LE and TE solutions also provide pH balance at a desired pH. In certain embodiments, the TE solution is a 12.5 mM Tris-HEPES buffer solution having pH of about 8. In some embodiments, the LE solution is a 1000 mM Tris and 400 mM tartrate solution having a pH of about 8. In other embodiments, the LE solution includes 700 mM Tris and 280 mM tartrate. Other TE and LE solutions may be used without departing from the scope hereof.

In a Step 320, a mixed-cell sample is provided. In an example of Step 320, the mixed-cell sample includes more than one cell type, including a target cell type to be captured and at least one other cell type (e.g., a non-target cell type). The mixed-cell sample may be provided in a variety of ways. For example, for samples received from a sexual assault kit, one or more buccal swabs may be immersed in a predetermined volume (e.g., 500 µL) of the TE solution to suspend the cells. For testing purposes, mixed-cell samples may be prepared by combining epithelial cells from buccal swabs of healthy volunteers with sperm cells obtained from a cryobank facility. The sperm cells are centrifuged and resuspended in the TE solution, then mixed with the solution of epithelial cells. Alternatively, the cells can be resuspended in the TE sample slurry from raw semen (without washing).

In certain embodiments, the mixed-cell sample is stored undisturbed to allow for cell settling. Depending on the type of target cells and the type of non-target cells, cell settling may be used to assist with cell separation if the non-target cells settle at a faster rate than the target cells. For example, epithelial cells tend to settle more rapidly than sperm cells, which can aid in Steps 330 and 340 described below for focusing and extracting sperm cells, respectively. In some embodiments, the mixed-cell sample is stored undisturbed for fifteen minutes to enable cell settling prior to focusing.

In a Step 330, the target cells are focused at the LE/TE interface. In an example of step 330, sperm cells are focused at the LE/TE interface. Focusing is performed by expelling a small amount of the LE solution in the capillary into the mixed-cell sample, and concurrently applying a voltage which causes the target cells to migrate to the LE/TE interface. For example, capillary 130 and second electrode 162 are inserted into mixed-cell sample container 140 as depicted in FIG. 2A. Pump 120 increases pressure gradually by about 700 Pa to move LE solution from LE reservoir 110 such that a small amount of LE solution is expelled from capillary 130 into the mixed-cell sample, and a pressure-driven counterflow is provided through capillary 130. Concurrently, the voltage is raised (e.g., by about 1000V to 2000V) in the mixed-cell sample via first and second electrodes 161, 162. The gradually increasing pressure and voltage differential are maintained for a predetermined duration for focusing to occur. Focusing for too little time fails to accumulate a substantial number of target cells at the LE/TE interface. Too much time focusing may lead to clogging of the capillary.

In a Step 340, the target cells are extracted from the sample container into the capillary. In other words, cells that were focused at the LE/TE interface in Step 330 are pulled into the capillary. For example, as depicted in FIG. 2B, a moderate negative hydrodynamic pressure (P) that ramps from the pressure at focusing to about −2500 Pa is applied from pump 120 to draw focused cells 170 upwards into capillary 130 to the region adjacent detector 150.

In an optional Step 350, the target cells are detected. In an example of Step 350, a non-invasive method is used to detect the presence of target cells in capillary 130. In certain embodiments, capillary 130 may be threaded through a conductivity detector (e.g., $C^4D$) that detects the transition between the LE solution and the TE solution as the LE/TE interface is pulled past detector 150. Thus, the conductivity detector indirectly detects the presence of the focused target cells. In some embodiments, direct detection of the target cells is performed (e.g., using a LIF detector). However, LIF detection generally requires staining the target cells with light-excitable dye, which may preclude certain downstream analysis (e.g., DNA-intercalation of the dye may prevent DNA sequencing or another DNA analysis).

In a Step 360, the target cells are expelled into a separate receptacle. As depicted in FIG. 2D, sample container 140 is replaced with receptacle 142. A large positive hydrodynamic pressure (P) of about 4000 Pa is applied by pump 120 to expel target cells 170 into receptacle 142. To prepare the target cells for subsequent analysis, receptacle 142 may contain a buffer solution (e.g., to maintain viability of the target cells) or a preservation solution to preserve the target cells.

Following Step 360, the target cells may be visualized and counted. In certain embodiments, approximately 0.1 μL to about 0.5 μL of extracted cells are deposited or transferred to a microscope slide and heat-fixed. The smear of cells is stained to facilitate counting. For example, for staining sperm cells, a Christmas tree staining protocol may be used, in which picroindicarmine is used to stain the tails of the sperm in blue and nuclear fast red is used to stain the heads of the sperm a bright purple/pink. After staining, the microscope slides are dried (e.g., under laboratory ambient conditions), subjected to 2.5 μL of water, and covered with a cover slip. The slides are viewed under a microscope (e.g., at 4×, 10×, and/or 40× magnification) and the cells are counted. Alternatively, the cells may be counted using digital imaging combined with software recognition. In some embodiments, the number of extracted sperm and epithelial cells are compared to counts of samples obtained from aliquots prior to extraction. Cells from these aliquots may also be stained for counting as described above.

According to a working example of method 300, mixed-cell samples were prepared from ten buccal swabs that were suspended in the TE solution (e.g., 12.5 mM Tris-HEPES buffer solution) and slurried with a 1:1000 dilution of sperm cells from a cryobank sample. Sperm cells were extracted using a 30 μm ID capillary. The LE solution was 700 mM Tris and 280 mM tartrate. Prior to beginning the extraction protocol, cells in the mixed-cell sample were allowed to settle for 15-minutes. Focusing of the sperm cells was performed for 10 min and the maximum current was approximately 30 μA. Epithelial and sperm cells were counted from a pre-extraction aliquot and from seven extracted samples (n=7). Average values plus/minus one standard deviation are shown in Table 1 after rounding to the nearest whole number.

TABLE 1

| Extractions using a 30 μm ID capillary. | | | | |
|---|---|---|---|---|
| Cell Counts | Epithelial Cells | | Sperm Cells | |
| n = 7 | Average | Std Dev | Average | Std Dev |
| Pre-extraction | 229 | 34 | 16 | 14 |
| Post-extraction | 5 | 8 | 27 | 28 |

The results shown in Table 1 indicate that only a very small number of epithelial cells (5±8) were extracted and a larger number of sperm cells (27±28) were extracted despite the pre-extraction aliquot having a much higher number of epithelial cells (229±34) compared to sperm cells (16±14). Ideally, the extracted samples would contain zero epithelial cells and an even higher number of sperm cells. Although other extraction conditions could possibly be improved while using a 30 μm inner diameter (ID) capillary, a capillary having a smaller ID was investigated, as described below.

According to another working example of method 300, mixed-cell samples were prepared from ten buccal swabs that were suspended in the TE solution and slurried with a 1:1000 dilution of sperm cells from a cryobank sample. Sperm cells were extracted using a 24 μm ID capillary. The LE solution was 1000 mM Tris and 400 mM tartrate. Prior to beginning the extraction protocol, cells in the mixed-cell sample were allowed to settle for 15 minutes. Focusing of the sperm cells was performed for 10 minutes and the maximum current was approximately 15 μA. Epithelial and sperm cells were counted from a pre-extraction aliquot and from seven extracted samples. Average values plus/minus one standard deviation are shown in Table 2 after rounding to the nearest whole number.

TABLE 2

| Extractions using a 24 μm ID capillary and 15-minutes of settling. | | | | |
|---|---|---|---|---|
| Cell Counts | Epithelial Cells | | Sperm Cells | |
| n = 7 | Average | Std Dev | Average | Std Dev |
| Pre-extraction | 352 | 120 | 27 | 15 |
| Post-extraction | 2 | 4 | 67 | 29 |

The results shown in Table 2 indicate that fewer epithelial cells (e.g., 2±4) were extracted and an increased number of sperm cells (e.g., 67±29) were extracted compared to using a 30 μm ID capillary as described above, despite having comparable numbers of epithelial cells and sperm cells pre-extraction. Since such a small number of epithelial cells were extracted, one possibility is that they adhered to the outside of the capillary or the electrode and were then transferred from the capillary or the electrode to the microscope slide for counting, rather than the epithelial cells having been focused with the sperm cells. While the smaller ID capillary showed improvement, other conditions may also be altered to improve the results, as described below.

According to yet another working example of method 300, mixed-cell samples of 1× buccal swabs were slurried with a 1:1000 dilution of sperm cells in the TE solution. Sperm cells were extracted using a 24 µm ID capillary. The LE solution was 1000 mM Tris and 400 mM tartrate. Prior to beginning the extraction protocol, cells from half of the mixed-cell samples (n=3) were allowed to settle for 15-minutes while the other half of the mixed-cell samples (n=3) were not allowed a setting time (unsettled). Focusing of the sperm cells was performed for 10 minutes. Epithelial and sperm cells were counted from a pre-extraction aliquot and from six extracted samples (three settled and three non-settled). Average values plus/minus one standard deviation are shown in Table 3 after rounding to the nearest whole number.

TABLE 3

Comparison of unsettled versus settled samples using a 24 µm ID capillary.

| Cell Counts | Epithelial Cells | | Sperm Cells | |
|---|---|---|---|---|
| n = 3 | Average | Std Dev | Average | Std Dev |
| Pre-extraction (n-1) | 87 | — | 17 | — |
| Post-extraction, unsettled | 14 | 12 | 39 | 7 |
| Post-extraction, settled | 2 | 3 | 67 | 27 |

The results shown in Table 3 indicate that cell settling lowered the number of epithelial cells and increased the number of sperm cells extracted (the second row versus the third row). This was expected since separate optical density experiments (not shown) indicated substantial settling of epithelial cells and minimal settling of sperm cells during a settling time of fifteen minutes. The results from the settled samples (third row) were similar to those shown in FIG. 3, as expected, despite the mixed-cell sample beginning with fewer epithelial cells (87), due to only one buccal swab being used, and a comparable number of sperm cells (17). For example, 2±3 epithelial cells were extracted and 67±27 sperm cells were extracted following settling.

According to yet another working example of method 300, mixed-cell samples of 1× buccal swabs were slurried with a 1:1000 dilution of sperm cells in the TE solution. Sperm cells were extracted using a 24 µm ID capillary. The LE solution was 1000 mM Tris and 400 mM tartrate. Prior to beginning the extraction protocol, cells in the mixed-cell sample were allowed to settle for 15-minutes. Focusing of the sperm cells was performed for 5-minutes. Epithelial and sperm cells were counted from a pre-extraction aliquot and from ten extracted samples. Average values plus/minus one standard deviation are shown in Table 4 after rounding to the nearest whole number.

TABLE 4

Extraction using a 24 µm ID capillary with 15-minutes of settling and 5-minutes of focusing.

| Cell Counts | Epithelial Cells | | Sperm Cells | |
|---|---|---|---|---|
| n = 10 | Average | Std Dev | Average | Std Dev |
| Pre-extraction | 62 | 39 | 12 | 5 |
| Post-extraction | 0 | 0 | 32 | 16 |

The results shown in Table 4 indicated that no epithelial cells were present in the extracts, while 32±16 sperm cells were extracted. The shorter focusing time may have contributed to the reduction in both epithelial cells and sperm cells that were extracted. A slightly longer focusing time may increase the yield of extracted sperm cells without introducing epithelial cells.

According to yet another working example of method 300, mixed-cell samples of 1× buccal swabs were slurried with a 1:1000 dilution of sperm cells in the TE solution. Sperm cells were extracted using a 24 µm ID capillary. The LE solution was 1000 mM and 400 mM tartrate. Prior to beginning the extraction protocol, cells in the mixed-cell sample were allowed to settle for 15-minutes. Also prior to each extraction, the capillary was precoated with a surface passivation agent (e.g., by dipping the capillary in the agent solution) to reduce cell adhesion to the capillary. In certain embodiments, the surface passivation agent solution is a solution containing 0.1-1% polyvinylpyrrolidone (PVP). Focusing of the sperm cells was performed for about 7-minutes. Epithelial and sperm cells were counted from a pre-extraction aliquot and from three extracted samples. Average values plus/minus one standard deviation are shown in Table 5 after rounding to the nearest whole number.

TABLE 5

Extractions using a 24 µm ID capillary precoated with PVP, 15-minutes of settling and 7-minutes of focusing.

| Cell Counts | Epithelial Cells | | Sperm Cells | |
|---|---|---|---|---|
| n = 3 | Average | Std Dev | Average | Std Dev |
| Pre-extraction | 132 | 38 | 13 | 13 |
| Post-extraction | 0 | 0 | 69 | 19 |

Similar to the results shown in Table 4, the results shown in Table 5 also indicated that no epithelial cells were present in the extracts. However, an increased number of sperm cells (69±19) were extracted compared to the results shown in Table 4 (only 32±16) indicating a further improvement.

It should be appreciated that, while the above disclosure has been generally directed to the field of separating sperm cells from epithelial cells (e.g., for use by forensics labs processing sexual assault kits), embodiments of this disclosure may be directed to other fields and uses. For example, embodiments of the cell extraction methods described herein may be used to extract other types of cells from mixed-cell samples by adjusting various parameters such as the LE and TE solutions, focusing time, maximum current, capillary ID, etc.

Although embodiments of this disclosure have been described with reference to the illustrations in the attached drawing figures, it is noted that equivalents may be employed and substitutions made herein without departing from the scope hereof as recited in the claims.

Having thus described various embodiments, what is claimed as new and desired to be protected by Letters Patent includes the following:

1. A cell extraction method, comprising:
   providing a mixed-cell sample in a sample container, the mixed-cell sample having both target cells and non-target cells slurried in a trailing-electrolyte solution;
   providing a leading-electrolyte solution in a capillary, the capillary having an inlet and an outlet, the inlet being coupled with a pressure control device and the outlet being disposed in the sample container;
   focusing the target cells at an interface between the leading-electrolyte solution and the trailing-electrolyte solution by applying a positive pressure to the inlet of the capillary via the pressure control device, and by concurrently applying an electric field along the length of the capillary via electrodes;

extracting the target cells from the sample container and into the capillary by applying a negative pressure to the inlet of the capillary; and expelling the target cells into a receptacle by transferring the capillary from the sample container to the receptacle and then applying a positive pressure to the inlet with the pressure control device.

2. The cell extraction method of claim 1, further comprising detecting the target cells in the capillary prior to expelling the target cells into the receptacle.

3. The cell extraction method of claim 2, wherein detecting the target cells comprises detecting the interface between the leading electrolyte and the trailing electrolyte using a conductivity detector.

4. The cell extraction method of claim 2, wherein detecting the target cells comprises detecting the cells with a laser-induced fluorescence detector.

5. The cell extraction method of claim 1, further comprising storing the mixed-cell sample undisturbed for a predetermined duration prior to focusing the target cells to assist cell separation due to settling of the non-target cells at a faster rate than the target cells.

6. The cell extraction method of claim 1, the step of focusing the target cells further comprising:

expelling a small amount of the leading electrolyte solution from the capillary into the mixed-cell sample; and providing pressure-driven counterflow of the leading electrolyte solution through the capillary.

7. The cell extraction method of claim 1, wherein focusing of the target cells is performed for about three minutes to about twenty minutes.

8. The cell extraction method of claim 1, wherein a maximum electrical current during focusing is from about 5 µA to about 50 µA.

9. The cell extraction method of claim 1, further comprising dipping the capillary in a surface passivation agent solution to reduce cell adhesion to the capillary prior to the outlet of the capillary being placed in the sample container.

10. The cell extraction method of claim 1, wherein providing the mixed-cell sample includes providing cells from a buccal swab slurried in the trailing electrolyte solution.

11. The cell extraction method of claim 1, wherein the target cells are sperm cells and the non-target cells include epithelial cells.

12. The cell extraction method of claim 1, wherein the leading electrolyte solution has a Tris concentration from about 100 mM to about 2000 mM and a tartrate concentration from about 100 mM to about 1000 mM, and the trailing electrolyte solution is a Tris-HEPES buffer solution having a Tris concentration from about 5 mM to about 100 mM and a HEPES concentration from about 5 mM to about 100 mM.

13. The cell extraction method of claim 1, wherein the capillary has an inner diameter from about 10-microns to about 50-microns.

14. A cell extraction system for use with a gradient elution isotachophoresis method, comprising:

slurrying a mixed-cell sample containing target cells and non-target cells in a trailing electrolyte solution, the trailing electrolyte solution being adapted to migrate slower than the target cells;

providing a leading electrolyte solution to a separation path in fluid contact with the trailing electrolyte solution, the leading electrolyte solution being adapted to migrate faster than the target cells;

applying an electric field along the separation path to focus the target cells at the interface between the leading-electrolyte solution and the trailing electrolyte solution;

extracting the target cells into the separation path; and expelling the target cells from the separation path into a container.

15. The cell extraction method of claim 14, wherein the separation path comprises a capillary, the capillary having an inner diameter from about 10-microns to about 30-microns.

16. The cell extraction method of claim 15, wherein the capillary has an inner diameter of about 24-microns.

17. The cell extraction method of claim 15, further comprising precoating the capillary with a surface passivation agent to prevent cells from adhering to the separation path.

18. The cell extraction method of claim 17, wherein the surface passivation agent contains polyvinylpyrrolidone.

19. A cell extraction electrolyte solution for use with a gradient elution isotachophoresis method, comprising:

a trailing electrolyte solution adapted to migrate slower than target cells while using the gradient elution isotachophoresis method, wherein a mixed-cell sample containing the target cells and non-target cells is slurried in the trailing electrolyte solution prior to cell extraction;

a leading electrolyte solution adapted to migrate faster than the target cells while using the gradient elution isotachophoresis method, wherein the leading electrolyte solution is provided to a separation path in fluid contact with the trailing electrolyte solution; and the leading electrolyte solution has a Tris buffer concentration from about 100 mM to about 2000 mM and a tartrate concentration from about 100 mM to about 1000 mM.

20. The cell extraction electrolyte solution of claim 19, wherein the trailing electrolyte solution has a Tris buffer concentration from about 5 mM to about 100 mM and a HEPES concentration from about 5 mM to about 100 mM.

* * * * *